United States Patent [19]

Sharma

[11] Patent Number: 6,030,777
[45] Date of Patent: Feb. 29, 2000

[54] RECOMBINANT VECTORS

[75] Inventor: Umender Sharma, Bangalore, India

[73] Assignee: Astra Aktiebolag, Sodertalje, Sweden

[21] Appl. No.: 08/875,229

[22] PCT Filed: May 7, 1997

[86] PCT No.: PCT/SE97/00763

§ 371 Date: Jul. 18, 1997

§ 102(e) Date: Jul. 18, 1997

[87] PCT Pub. No.: WO98/03666

PCT Pub. Date: Jan. 29, 1998

[30] Foreign Application Priority Data

May 17, 1996 [IN] India ............................... 829/MAS/96
Jul. 18, 1996 [SE] Sweden ................................ 9602803
Sep. 10, 1996 [SE] Sweden ................................ 9603282

[51] Int. Cl.$^7$ ........................................................ C12Q 1/68
[52] U.S. Cl. ................................. 435/6; 435/7.1; 435/29; 536/23.1; 536/23.7
[58] Field of Search ........................... 435/6, 69.1, 320.1, 435/71.1, 71.2, 252.33, 252.3, 7.1, 29; 536/23.1, 24.1

[56] References Cited

U.S. PATENT DOCUMENTS 5,300,431   4/1994   Pierce et al. .................................. 435/6

FOREIGN PATENT DOCUMENTS

4204103 A1   8/1993   Germany .
WO9214819   9/1992   WIPO .

OTHER PUBLICATIONS

Orsini, et al., Journal of Bacteriology 175, 85–93 (1993).
Studier, et al., Methods in Enzymology 185, 60–89 (1990).
Ozaki, et al., Gene 8, 301–314 (1980).
Chang, et al., Journal of Bacteriology 134, 1141–1156 (1978).
Cheng, et al., Journal of Bacteriology 154, 1005–1008 (1983).
Burgess, et al., Biochemistry 14, 4634–4639 (1975).
Kuhn, et al., Gene 44, 253–263 (1986).
Henrich, et al., Gene 42, 345–349 (1986).
Amann, et al., Gene 69, 301–315 (1988).
Burns, et al., Gene 27, 323–325 (1984).
Wang, et al., Gene 100, 195–199 (1991).
Gay, et al., Journal of Bacteriology 164, 918–921 (1985).
Ohnishi, et al., Molecular Microbiology 6, 3149–3157 (1992).
Duncan, et al., Proc. Natl. Acad. Sci. USA 90, 2325–2329 (1993).
Benson, et al., Proc. Natl. Acad. Sci. USA 90, 2330–2334 (1993).
Schumann, Molec. Gen. Genet. 174, 221–224 (1979).
Roberts, et al., Gene 12, 123–127 (1980).
Honigman, et al., Gene 13, 289–298 (1981).
Dean, Gene 15, 99–102 (1981).
Covarrubias, et al., Gene 17, 79–89 (1982).
Hagan, et al., Gene 19, 147–151 (1982).
Hennecke, et al., Gene 19, 231–234 (1982).

*Primary Examiner*—David Guzo
*Assistant Examiner*—Jon Shuman
*Attorney, Agent, or Firm*—White & Case LLP

[57] ABSTRACT

The present invention relates to recombinant vectors which are useful for direct selection of colonies harboring recombinant plasmids, on basis of the loss of expression of a gene coding for an AsiA polypeptide from *E. coli* bacteriophage T4, the expression of which would normally have resulted in toxicity to the bacterial host. The invention also relates to host cells harboring the vectors, as well as to methods utilizing the vectors, for the selection of nucleic acid clones.

13 Claims, 2 Drawing Sheets

RECOMBINANT VECTORS

TECHNICAL FIELD

The present invention relates to recombinant vectors which are useful for direct selection of colonies harboring recombinant plasmids, on basis of the loss of expression of a known gene, the expression of which would normally have resulted in toxicity to the bacterial host. The invention also relates to host cells harboring the said vectors, as well as to methods utilizing the said vectors, for the selection of nucleic acid clones.

BACKGROUND ART

Antisigma Factors

In eubacteria, the core RNA polymerase is composed of α, β, and β' subunits in the ratio 2:1:1. To direct RNA polymerase to promoters of specific genes to be transcribed, bacteria produce a variety of proteins, known as sigma (σ) factors, which interact with RNA polymerase to form an active holoenzyme. The resulting complexes are able to recognize and attach to selected nucleotide sequences in promoters.

Antisigma (Asi) proteins, i.e. proteins which inhibit the sigma subunit of RNA polymerase, are known in the art. A gene called asiA, coding for the 10 kDa anti-sigma$^{70}$ factor of bacteriophage T4 (hereinafter referred to as AsiA), has been identified by Orsini et al. (1993) J. Bacteriol. 175, 85–93. The open reading frame encoded a 90 amino acid protein having the deduced sequence shown as SEQ ID NO: 1.

The asiA-encoded protein was overproduced in a phage T7 expression system and partially purified. It showed a strong inhibitory activity towards sigma$^{70}$-directed transcription by RNA polymerase holoenzyme. The nucleotide sequence of gene asiA has been deposited in the GenBank data base under accession no. M99441.

Examples of proteins regulating the sigma subunit of RNA polymerase are known from other systems such as *Salmonella typhimurium* (Ohnishi et al. (1992) Mol. Microbiol. 6, 3149–3157) and *Bacillus subtilis* (Duncan & Losick (1993) Proc. Natl. Acad. Sd. U.S.A. 90, 2325–2329; Benson & Haldenwang (1993) Proc. Natl. Acad. Sci. U.S.A. 90, 2330–2334). The nucleotide sequences of these antisigma factors do not show any gross similarity with the asiA sequence disclosed by Orsini et al. Therefore, although the different antisigma factors are functionally similar, it is not possible to anticipate that an antisigma factor from *E. coli* will neutralize a RNA polymerase sigma subunit from another bacterial species.

Selection Vectors

Recombinant DNA technology has led to the development of a variety of vectors that enable cloning and expression of heterologous genes. Generally, the heterologous genes are engineered in such a way that a known marker gene is either interrupted or replaced by the gene. Correct recombinants are selected by screening transformants for the loss of the said marker. This requires screening several hundreds of colonies for the loss of the marker gene. In addition, several of the selected clones generally turn out to be false positives for a variety of reasons.

In order to overcome these disadvantages, researchers have developed vectors that enable a direct positive selection of correct recombinants. Generally, such vectors harbor a gene wherein the encoded product on expression is toxic to the host. This toxicity could be lethal to the host thereby killing the organism or render the host cells to be sick. When a heterologous gene interrupts or replaces the toxic gene, the resulting recombinant grows normally in solid media.

Positive selection vectors, useful for direct selection of colonies harboring recombinant plasmids, are thus known in the art, e.g. from:

U.S. Pat. No. 5,300,431;
Burns and Beacham, Gene 27 (1984) 323–325;
Kuhn et al., Gene 42 (1986) 253–263;
Heinrich and Plapp, Gene 42 (1986) 345–349;
Gay et al., J. Bacteriol. (1985) 918–921;
Cheng and Modrich, J. Bacteriol. (1983) 1005–1008;
Dean, Gene 15 (1981) 99–102;
Hagan and Warren, Gene 19 (1982) 147–151;
Hennecke et al., Gene 19 (1982) 231–234;
Honigman & Oppenheim, Gene 13 (1981) 289–298;
Ozaki et al., Gene 8 (1980) 801–314;
Roberts et al., Gene 12 (1980) 123–127;
Schumann, Molec. gen. Genet 174 (1979) 221–224

However, the use of an antisigma gene in a positive selection vector has not previously been described.

DISCLOSURE OF THE INVENTION

Figure 1:
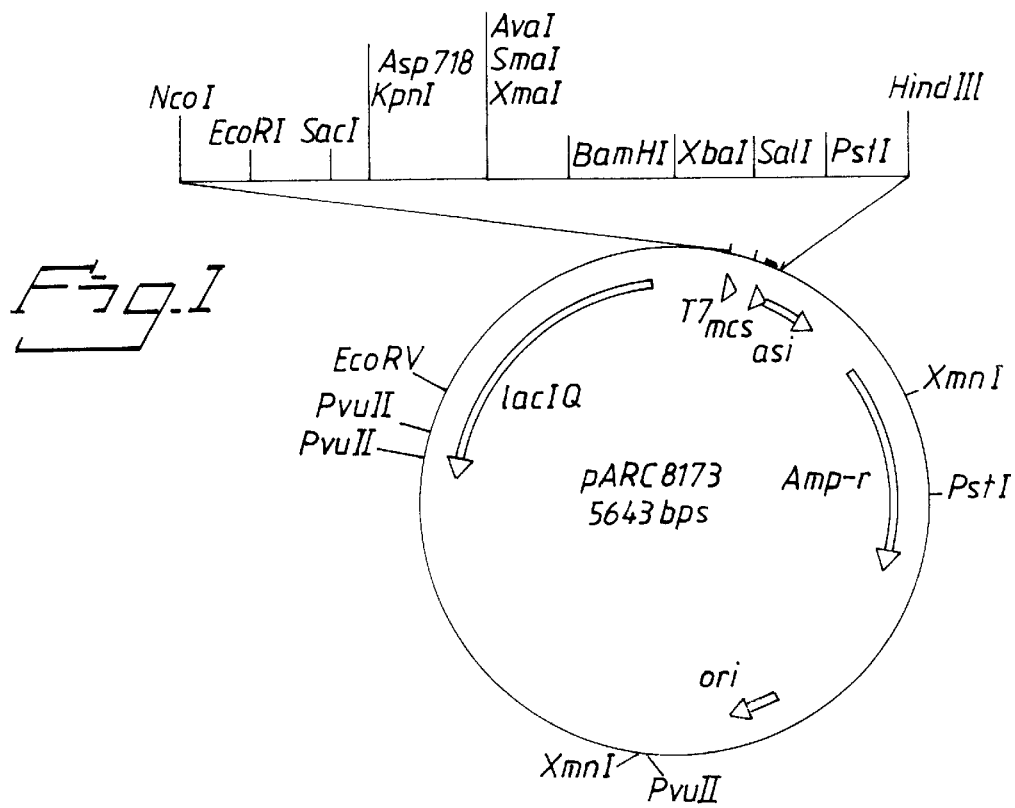
FIG. 1: Plasmid map of vector pARC 8173

The present invention provides a vector comprising a positive selection cassette, the said positive selection cassette comprising a DNA sequence coding for an antisigma polypeptide, said DNA sequence including a multiple cloning site for cloning of a heterologous gene. When a heterologous gene is cloned into the multiple cloning site, the expression of the normally toxic antisigma polypeptide is abolished. Consequently, a positive selection of clones harboring the heterologous gene is achieved.

Preferably, the said vector is a vector wherein the said antisigma polypeptide is an AsiA polypeptide from *E. coli* bacteriophage T4, having essentially the amino acid sequence shown as SEQ ID NO: 1 or SEQ ID NO: 2 in the Sequence Listing, or a functionally equivalent variant thereof.

In another preferred form, the said vector is a vector wherein the said DNA sequence encodes a polypeptide having essentially the amino acid sequence shown as SEQ ID NO: 4 in the Sequence Listing. It will thus be understood that the addition of the multiple cloning site to the gene coding for the AsiA protein will result in the expression of a polypeptide having additional amino acids as compared to the wild-type AsiA protein (cf. Example 6.3 below). It has been shown that such extra amino acids will not abolish the toxicity of the expressed polypeptide (cf. Example 3 below). However, the introduction of a heterologous gene into the cloning site will significantly reduce such toxicity so that a positive selection can be achieved.

It will be understood by the skilled person that the vector according to the invention comprises additional features which allows the vector to be used for the expression of a desired protein. Such features can e.g. include
a suitable antibiotic selection marker;
an origin of replication;
a promoter sequence, such as a T7 Φ10 promoter sequence, operatively linked to the said DNA sequence coding for an AsiA polypeptide. The term "operatively linked" as used herein means that the promoter is linked with a structural gene in the proper frame to express the structural gene under control of the promoter.

In another aspect, the invention provides a host cell harbouring a vector as described above. The host cell can e.g. be an *E. coli* cell. However, it has surprisingly been found that the AsiA protein is capable of binding to sigma$^{70}$ factors of other bacterial species, such as *Salmonella typhimurium*. It is thus foreseen that the positive selection vector according to the invention will be useful also in *S. typhimurium* and other host cells which are suitable for heterologous cloning. A positive selection vector useful in *S. typhimurium* will be a construct comprising the asiA gene along with a broad host range replicon such as RSF 1010.

A further aspect of the invention is a method of positive selection of nucleic acid clones, comprising
(a) cloning a DNA fragment into a vector which comprises a DNA sequence coding for an antisigma polypeptide, said DNA sequence including a multiple cloning site for cloning of a heterologous gene;
(b) inserting the vector into a suitable host cell; and
(c) growing the host cell under suitable conditions.

In a preferred form of the invention, the said vector is a vector according to the invention as specified above. The said host cell can be e.g. an *E. coli* cell or a *Salmonella typhimurium* cell.

Throughout this description and in particular in the following examples, the terms "standard protocols" and "standard procedures", when used in the context of molecular cloning techniques, are to be understood as protocols and procedures found in an ordinary laboratory manual such as: Sambrook, J., Fritsch, E. F. and Maniatis, T. (1989) Molecular Cloning: A laboratory manual, 2nd Ed., Cold Spring Harbor Laboratory Press, Cold Spring Harbor, N.Y.

EXAMPLES

Example 1

Cloning of the asiA Gene

The coding sequence for the asiA gene (Orsini et al., supra) was amplified from the genomic DNA of bacteriophage T4 by PCR using standard methods. The 5'-primer included the sequence of the restriction enzyme NcoI while the 3'-primer included the sequence for the restriction enzyme BamHI. The amplified fragment was ligated to NcoI-BamHI restricted pBR 329 (Covarrubias (1982) Gene 17,79–89) and transformed into competent *E. coli* DH5α cells. Recombinants were selected at +37° C. as chloramphenicol sensitive, ampicillin resistant transformants. One of the transformants having the desired restriction pattern was labelled pARC 8100.

The inclusion of the sequence encoding NcoI resulted in the change of the second amino acid from asparagine to glycine (SEQ ID NO: 2). The nucleotide sequence of the asiA gene cloned in pARC 8100 was verified by double stranded sequencing and found to be identical to the asiA sequence as disclosed by Orsini et al., except for the expected change of codon for the second amino acid as a result of the PCR cloning protocol used.

Example 2

In Vivo Toxicity of asiA Product in *E. coli*

2.1

The NcoI-BamHI DNA fragment from pARC 8100 was ligated to pET 8c (Kmr) (Studier et al. (1990) Methods Enzymol. 185, 60–89) and kanamycin resistant transformants with *E. coli* DH5α were selected at +37° C. One of the transformants harboring a plasmid with the expected restriction enzyme profile was labelled pARC 8115. pARC 8115 plasmid DNA was then used to transform the expression host *E. coli* BL26(DE3) and transformants selected both at +37° C. and at +30° C. However, no viable transformants could be obtained at either of the temperatures. The leaky expression from the T7 promoter in pET 8c being much higher than from pET 11d (Kmr) (Studier et al., supra) the toxicity of the asiA product could explain the non-transformability.

Transformants could however be obtained using *E. coli* BL21(DE3)/pLysS (Studier et al., supra) as host, in which the leaky expression is additionally repressed by the T7 lysozyme expressed from pLysS.

2.2

The NcoI-BamHI 366 bp DNA fragment was obtained from pARC 8100 and ligated to the NcoI-BamHI sites of pET 11d (Kmr) and transformed into *E. coli* DH5α. Transformants were selected for kanamycin resistance. Plasmid preparations from individual transformants were digested with restriction enzymes and the correct transformant that released the 284 bp fragment after NcoI-BamHI digest was labelled pARC 8101. The transformants were selected at +37° C. and appeared normal. pARC 8101 DNA was then used to transform the expression host *E. coli* BL26(DE3) (Studier et al., supra) and transformants selected for kanamycin resistance both at +37° C. and at +30° C. The transformants obtained at +37° C. were morphologically sick and non-viable indicating the acute toxicity of the leaky expression of the asiA gene. In contrast, healthy colonies could be obtained when transformants were selected at +30° C. where the leaky expression from the T7 promoter can be expected to be negligible.

BL26(DE3)/pLysS colonies were healthy at +37° C. and +30° C. indicating that tight regulation of expression in the BL26(DE3)LysS strain was the reason for the non-toxicity of the asiA product in this strain.

Transformants obtained from *E. coli* DH5α were healthy both at +37° C. and +30° C. indicating that the gene when transformed into a non-expression host was non-toxic to the host.

2.3

The asiA gene was excised from pARC 8101 as a XbaI-BamHI DNA fragment to include the sequence for the ribosome binding site and ligated to the XbaI-BamHI cleaved low copy vector pWKS129 (Wang & Kushner (1991) Gene 100, 195) and the ligation mix transformed to *E. coli* DH5α. Recombinant plasmid harboring the asiA gene was identified by restriction profile and labelled pARC 8114. This plasmid DNA when transformed into *E. coli* BL21(DE3) gave viable transformants both at +37° C. and +30° C. This is because the low copy number of the plasmid reduces the level of the AsiA protein expressed through leaky expression.

Example 3

Cloning of Fusion Protein in *E. coli*

The coding sequence for the asiA gene was excised as an NcoI-BamHI fragment from pARC 8100 and ligated to NcoI-BglII cleaved pARC 0499. The plasmid pARC 0499 (Deposited on Jun. 28, 1994 at The National Collections of Industrial and Marine Bacteria Limited (NCIMB), 23 St. Machar Drive, Aberdeen AB2, 1RY, Scotland, UK. under the Budapest Treaty with accession no. NCIMB 40664) has a NcoI site in frame with the glutathione-S-transferase encoding sequence, enabling fusion of the N-terminus of asiA sequences. The ligation mix was transformed into *E. coli* DH5a and transformants selected at +37° C. and +30° C. Viable colonies were obtained at both temperatures indicating the N-terminal fusion reduces the toxicity of the protein. The recombinant plasmid obtained with the sequences encoding GST-AsiA was labelled pARC 8105.

The construct pARC 8105 when transformed into DH5α yielded healthy colonies both at +37° C. and at +30° C. When pARC 8105 was transformed into BL26(DE3) the result was healthy colonies at +30° C., but sick colonies at +37° C. Consequently, it was surprisingly found that the GST fusion construct retained the toxicity of the AsiA product. This also suggests that addition of extra amino acids at the N-terminal of the AsiA protein does not lead to loss of activity. This was an important observation for the construction of a positive selection vector, since it is essential that the addition of nucleotide stretches in the form of a multiple cloning site should not alter the in vivo toxicity properties of the asiA gene product.

Example 4

4.1. Effect of *Salmonella typhimurium* sigma$^{70}$ on *E. coli* Transcription

The *E. coli* RNA polymerase assay was standardized following the protocol of Orsini et al. (J. Bacteriol. 175, 85–93, 1993) using T4 phage DNA as template to quantify sigma$^{70}$ dependent transcription. *E. coli* RNA polymerase core enzyme was purified following the protocol of Burgess and Jendriask (1975) Biochemistry 14, 4634–4638.

The RNA polymerase could be >80% inhibited by 0.07 μg of purified AsiA protein.

To a reaction mixture containing the *E. coli* RNA polymerase, T4 DNA and 0.1 μg of AsiA, increasing concentrations of purified *Salmonella typhimurium* sigma$^{70}$ was added and the RNA polymerase activity quantified. As shown in Table 1, addition of 4 μg of *S. typhimurium* sigma$^{70}$ could restore the activity of the RNA polymerase.

4.2. Preincubation of sigma$^{70}$ with AsiA

To a reaction mixture containing *E. coli* RNA polymerase and T4 DNA template there was added 0.1 μg AsiA and 4 μg *E. coli* or *S. typhimurium* sigma$^{70}$, preincubated at +37° C. for 10 min with 0.1 μg of AsiA. As shown in Table 1, preincubation of the sigma$^{70}$ with AsiA abolished the ability of the sigma$^{70}$, from both *E. coli* and *S. typhimurium*, to activate *E. coli* RNA polymerase.

TABLE 1

|  | E. coli sigma$^{70}$ | S. typhimurium sigma$^{70}$ |
|  | [$^3$H]UTP (nmol) | |
| --- | --- | --- |
| E. coli core RNA polymerase | 2.1 | 2.3 |
| E. coli core RNA polymerase + 0.1 mg AsiA | 0.57 | 0.34 |
| E. coli core RNA polymerase + 0.1 mg AsiA + 4 mg sigma$^{70}$ | 2.3 | 3.0 |
| E. coli core RNA polymerase + 0.1 mg AsiA + 4 mg sigma$^{70}$ (AsiA preincubated) | 0.68 | 0.98 |

Example 5
Construction of a Vector Wherein the asiA Gene is Replaced by a Gene for a Heterologous Protein The gene encoding α subunit of *E. coli* RNA polymerase was amplified from a standard *E. coli* strain by PCR, using a 5'-primer which introduced a NcoI site at the 5'-end of the PCR product; and a 3'-primer which introduced a BamHI site at the 3'-end of the PCR product.

The 1 kb PCR product was cut with NcoI and BamHI and cloned into pARC 8101 (an AsiA clone) at the NcoI-BamHI site essentially replacing the asiA gene with the new gene and transformed into *E. coli* BL 26(DE3). The construct was designated pARC 8113.

Six healthy colonies out of 100 sick colonies were recombinants carrying the plasmid encoding the gene for the a subunit of RNA polymerase. Consequently, a vector could be generated where loss of toxicity to the asiA gene indicated insertion of the desired gene into the cloning site.

Example 6
Construction of a Vector Harboring a Multiple Cloning Site for Cloning of any Heterologous Gene 6.1. Construction of pARC 8173

T4 chromosomal DNA was amplified by PCR using a 5'-primer having the sequence shown as SEQ ID NO: 5, which provided NcoI and HindIII sites at the 5'-end of the product. The 3'-primer, having the sequence shown as SEQ ID NO: 6, provided the loss of the EcoRI and introduction of EcoRV site at the 3'-end of the full length asiA gene.

The resulting 250 bp fragment was digested with NcoI-EcoRV and ligated to NcoI-EcoRV digested pBR 329 (Covarrubias (1982) Gene 17, 79–89). The construct was transformed into *E. coli* DH5α. The correct recombinant was identified by restriction digestion of plasmid preparations and identified as pARC 8169.

A 63 bp fragment which contained restriction sites for multiple restriction enzymes was obtained by digesting pTrc99A with NcoI-HindIII. The vector pTrc99A comprises a 55-bp EcoRI-HindIII polylinker fragment (Amann et al. (1988) Gene 69, 301). The said 63 bp fragment thus provided a multiple cloning site, which can be used for cloning of heterologous proteins, to the construct. The fragment was purified by known methods.

The plasmid pARC 8169 was digested with NcoI-HindIII and the major fragment was purified and ligated to the 63 bp fragment as obtained from pTRC 99A. The ligation mix was transformed into *E. coli* DH5α. The correct recombinant was selected by restriction digestion of the plasmid made by a miniprep and was identified as pARC 8172.

The plasmid pARC 8172 was digested with NcoI-EcoRV and the resulting 295 bp fragment was purified by standard methods and ligated to pET 11d (Studier et al., supra) digested with EcoRI, ends filled in by Klenow polymerase and again digested with EcoRI. The ligation mix was transformed into *E. coli* DH5α. The correct recombinant was identified by restriction of plasmid preparation of randomly selected transformants and was named as pARC 8173 (FIG. 1) (Deposited on Jan. 17, 1996 at The National Collections of Industrial and Marine Bacteria Limited (NCIMB), 23 St. Machar Drive, Aberdeen AB2, 1RY, Scotland, UK. under the Budapest Treaty under accession No. NCIMB 40784). The plasmid pARC 8173 was transformed into *E. coli* BL26(DE3) and the transformation yielded only sick colonies at +37° C. confirming that asiA gene was fully expressed in pARC 8173.

6.2. Construction of pARC 8177

Figure 2:
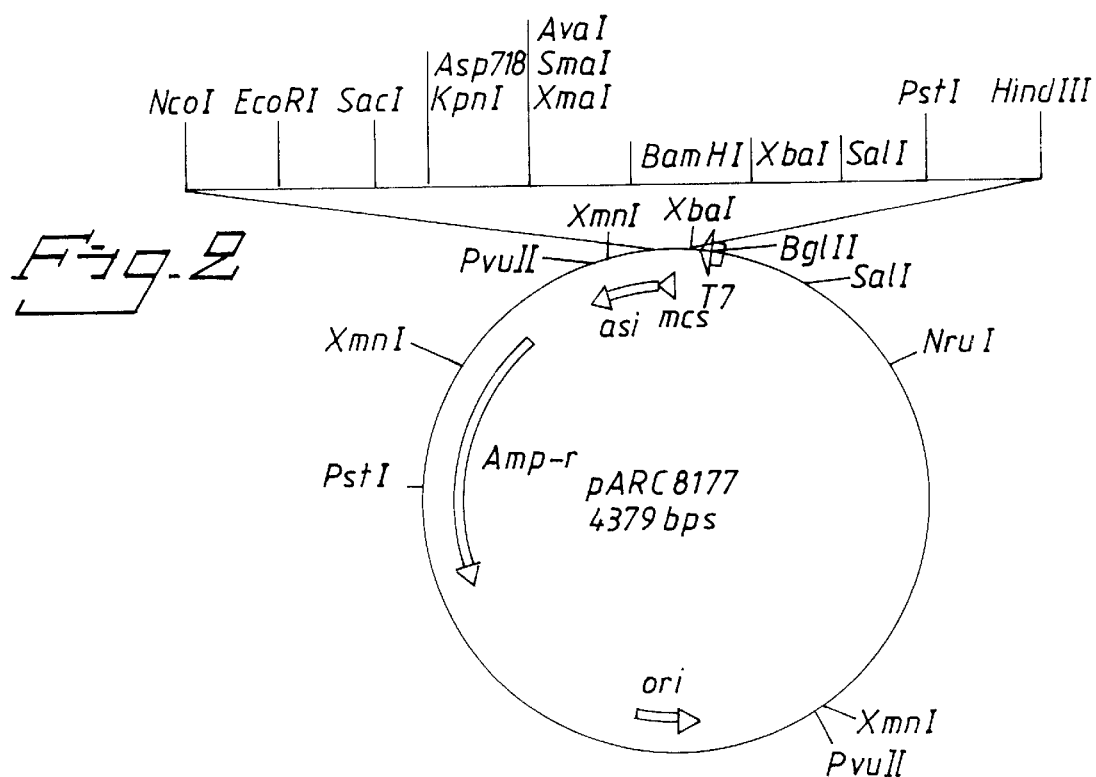
FIG. 2: Plasmid map of vector pARC 8177
Figure 3:
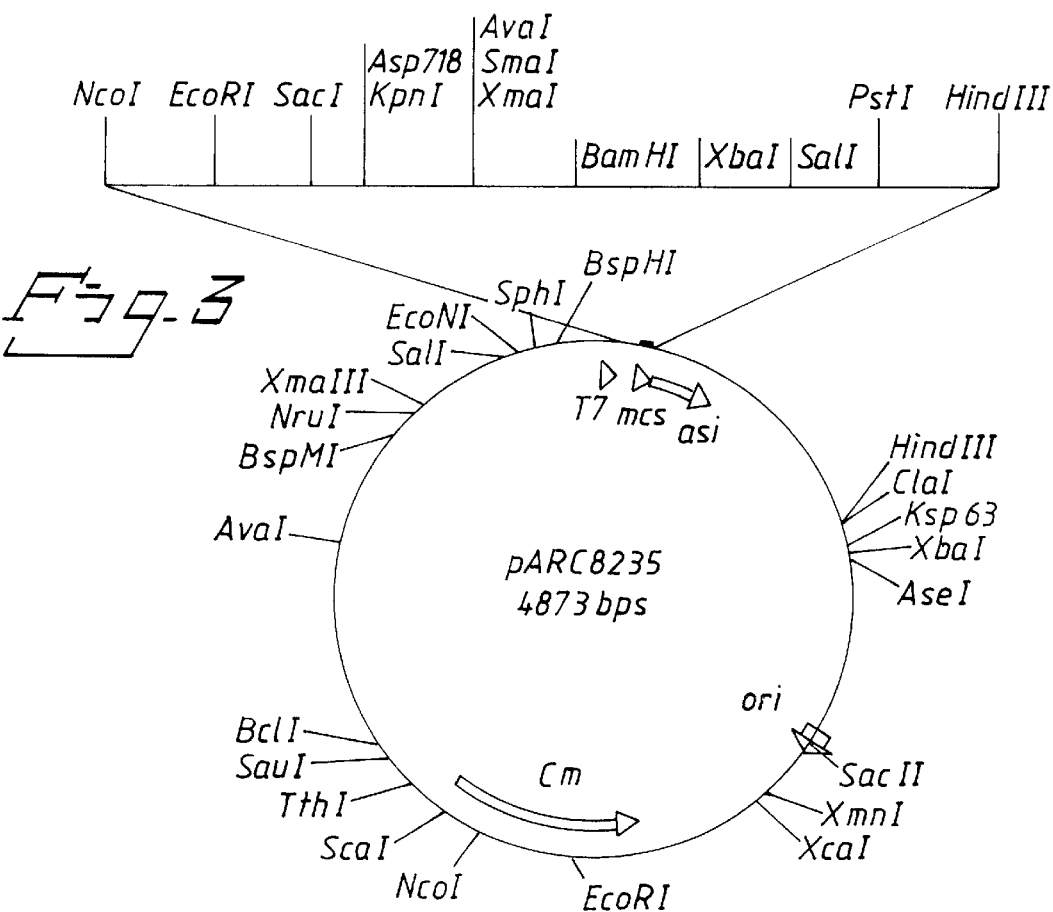
FIG. 3: Plasmid map of vector pARC 8235
Figure 4:
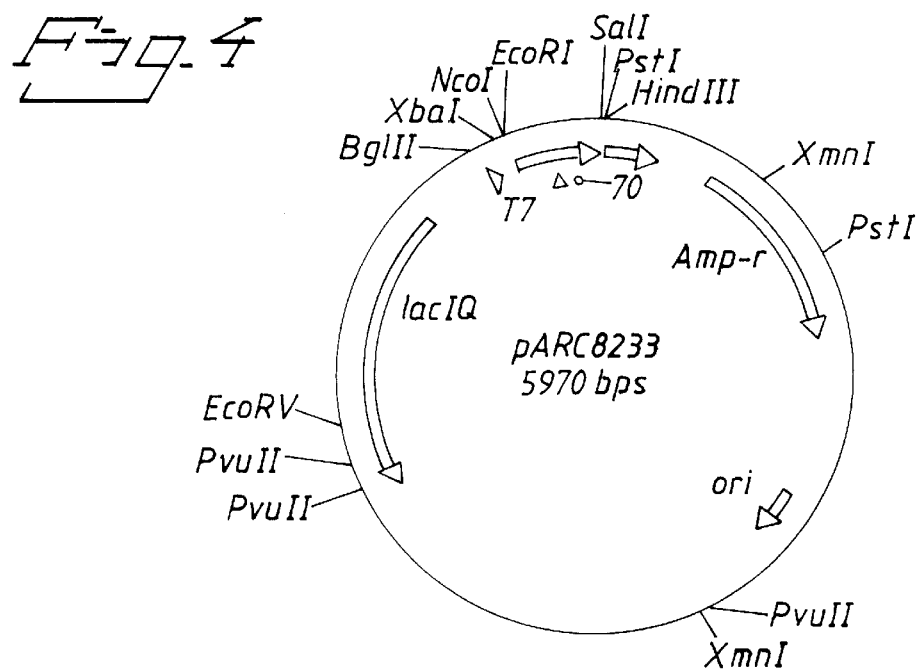
FIG. 4: Plasmid map of vector pARC 8233

Plasmid pET8c (Studier et al., supra) was digested with EcoRI, ends were filled using Klenow Polymerase and again digested with NcoI. This was ligated to the 295 bp NcoI-EcoRV fragment obtained from pARC 8172 (see above) and transformed into *E. coli* DH5α. Correct recombinant was identified by restriction analysis of plasmids obtained by mini prep analysis of several transformants and was identified as pARC 8177 (FIG. 2) (Deposited on Jan. 17, 1996 at The National Collections of Industrial and Marine Bacteria Limited (NCIMB), 23 St. Machar Drive, Aberdeen AB2, 1RY, Scotland, UK. under the Budapest Treaty under accession No. NCIMB 40785). The plasmid pARC 8177 was transformed into *E. coli* BL26(DE3) and the transformation yielded no colonies confirming that the asiA gene was fully expressed in pARC 8177.

6.3. Amino Acid Sequence of the Expressed AsiA Protein

As a result of the cloning procedure and the introduction of the multiple cloning site, additional amino acids are introduced in the AsiA protein expressed by pARC 8173 and pARC 8177. The N-terminal amino acid sequence "Met Asn Lys Asn Ile" (Residues 1–5 of SEQ ID NO: 1) has been replaced by "Met Glu Phe Glu Leu Gly Thr Arg Gly Ser Ser Arg Val Asp Leu Gln Ala Cys Lys Leu" (SEQ ID NO: 3; cf. Amann et al, supra). In addition, the ten C-terminal amino acids, corresponding to residues 81–90 of SEQ ID NO: 1, has been deleted as a result of the procedure. Consequently, the AsiA protein encoded by the asiA gene, to which the multiple cloning site has been added, has the amino acid sequence shown as SEQ ID NO: 4.

This addition of extra amino acids does not in itself lead to a loss of toxicity of the AsiA protein (cf. Example 3 above).

6.4. Use of pARC 8173 and 8177

The plasmids pARC 8173 and pARC 8177 are useful as recombinant vectors for cloning of heterologous proteins.

The plasmids pARC 8173 and pARC 8177 may be restricted with any of the restriction enzymes defined by the multiple cloning site as shown in FIGS. 1 and 2, respectively, and the heterologous gene suitably inserted using standard methods.

Correct transformants harboring the heterologous gene will be identified by transformation into *E. coli* BL21(DE3), since only host cells harboring pARC 8173 or pARC 8177 comprising the heterologous gene will grow as healthy colonies, while host cells harboring pARC 8173 or pARC 8177 without the heterologous gene will not grow at all, or grow as sick colonies.

The plasmids pARC 8173 and pARC 8177 are identical in terms of cloning facility. However, pARC 8173 possesses lac IQ and is thus more repressed in expression of AsiA or the heterologous gene. Therefore, either sick or healthy colonies are obtained after the cloning of heterologous genes. Addition of IPTG will kill sick colonies, while healthy colonies expressing heterologous genes are retained. In contrast, pARC 8177 will yield only healthy colonies when the heterologous gene, inserted in the asiA gene is expressed.

Preference of any one plasmid over the other would depend on the purpose. For cloning of a gene, either construct can be used. For the purpose of cloning and expressing a gene under a $T_7$ promoter, pET11d based pARC 8173 should be used, since the Φ10-Lac promoter is tightly regulated and the expression can be modulated by the addition of IPTG.

Example 7

Construction of a Positive Selection Vector Compatible with ColEI Based Vectors

ColEI based vectors are a series of vectors useful for cloning heterologous genes into *E. coli.* For this purpose, the 700 bp BglII-XmnI fragment from pARC 8173, encompassing the $T_7$ promoter and the asiA gene, was cloned into pACYC 184 (Chang, A. C. Y. and Cohen, S. N. (1978) J. Bacteriol. 134, 1141–1156) that has the p15A origin of replication. The resulting recombinant construct pARC 8235 (FIG. 3) was transformed into BL26(DE3). Transformation gave no colonies at +37° C., indicating the expression of the asiA gene.

Example 8

Use of a Positive Selection Vector in the Cloning of a Heterologous Gene 8.1. Use of pARC 8235

The construct pARC 8235 was used to test the principle of positive selection by the following procedure: pARC 8235 was digested with BamHI-HindIII and ligated to 1.1 kb BamHI-HindIII fragment from the construct pARC 0356, which encodes the mraγ gene of *E. coli,* and transformed into *E. coli* BL26(DE3). Recombinants were selected for chloramphenicol resistance (10 μg/ml) at +37° C. Correct clone was confirmed four out of six healthy colonies by restriction analysis of plasmids.

8.2. Use of pARC 8173

The 372 bp EcoRI-SalI fragment, encoding truncated $sigma^{70}$ of *E. coli* from pARC 8225, was ligated to EcoRI-SalI digested pARC 8173. Ligation mix was transformed into *E. coli* and transformants were selected on ampiciuin (50 μg/ml) at +37° C. Six healthy colonies were analyzed by restriction analysis. All six were found to be true recombinants. The construct was identified as pARC 8233 (FIG. 4).

Deposit of Microorganisms

The following plasmid vectors have been deposited under the Budapest Treaty at the National Collections of Industrial and Marine Bacteria (NCIMB), Aberdeen, U.K:

| Plasmid | Accession No. | Date of deposit |
|---|---|---|
| pARC 8173 | NCIMB 40784 | 17 January 1996 |
| pARC 8177 | NCIMB 40785 | 17 January 1996 |
| pARC 0499 | NCIMB 40664 | 28 June 1994 |

I claim:

1. A vector comprising a positive selection cassette, the positive selection cassette comprising a DNA sequence coding for an antisigma polypeptide, said DNA sequence including a multiple cloning site for cloning of a heterologous gene.

2. A vector according to claim 1 wherein the antisigma polypeptide is an AsiA polypeptide from *E. coli* bacteriophage T4, comprising the amino acid sequence shown as SEQ ID NO: 1 or SEQ ID NO: 2 in the Sequence Listing.

3. A vector according to claim 1 wherein the DNA sequence encodes a polypeptide comprising the amino acid sequence shown as SEQ ID NO: 4 in the Sequence Listing.

4. A vector according to claim 1 which is the plasmid vector pARC 8173 (NCIMB 40784), pARC 8177 (NCIMB 40785) or pARC 8235.

5. A host cell harbouring a vector according to any one of claims 1 to 4.

6. A host cell according to claim 5 which is an *E. coli* cell.

7. A host cell according to claim 5 which is a *Salmonella typhimurium* cell.

8. A method of positive selection of nucleic acid clones, comprising
   (a) cloning a DNA fragment into a vector which comprises a DNA sequence coding for an antisigma polypeptide, said DNA sequence including a multiple cloning site for cloning of a heterologous gene;
   (b) inserting the vector into a host cell; and
   (c) growing the host cell.

9. A method of positive selection of nucleic acid clones, comprising
   (a) cloning a DNA fragment into a vector which comprises a DNA sequence coding for an antisigma polypeptide, said DNA sequence including a multiple cloning site for cloning of a heterologous gene;
   (b) inserting the vector into a host cell; and
   (c) growing the host cell,
wherein the vector comprising a DNA sequence coding for an antisigma polypeptide is a vector according to any one of claims 1 to 4.

10. A method according to claim 8 wherein the host cell is an *E. coli* cell.

11. A method according to claim 8 wherein the host cell is a *Salmonella typhimurium* cell.

12. A method according to claim 9 wherein the host cell is an *E. coli* cell.

13. A method according to claim 9 wherein the host cell is a *Salmonella typhimurium* cell.

* * * * *

SEQUENCE LISTING

```
(1) GENERAL INFORMATION:

(iii) NUMBER OF SEQUENCES: 6

(2) INFORMATION FOR SEQ ID NO:1:

(i) SEQUENCE CHARACTERISTICS:
          (A) LENGTH: 90 amino acids
          (B) TYPE: amino acid
          (C) STRANDEDNESS:
```

-continued

```
         (D) TOPOLOGY: linear (ii) MOLECULE TYPE: protein (vi) ORIGINAL SOURCE:
         (A) ORGANISM: Bacteriophage T4

(x) PUBLICATION INFORMATION:
         (A) AUTHORS: Orsini, G
              Ouhammouch, M
              Le Caer, J-P
              Brody, E.N.
         (B) TITLE: The asiA gene of bacteriophage T4
              codes for
              the anti-sigma70 protein
         (C) JOURNAL: J. Bacteriol.
         (D) VOLUME: 175
         (F) PAGES: 85-93
         (G) DATE: 1993
         (K) RELEVANT RESIDUES IN SEQ ID NO:1: FROM 1 TO
              90

(xi) SEQUENCE DESCRIPTION: SEQ ID NO:1:

Met Asn Lys Asn Ile Asp Thr Val Arg Glu Ile Ile Thr Val Ala Ser
1               5                  10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Val Ser Glu Leu Thr Gln Glu
    50                  55                  60

Asp Lys Lys Thr Leu Ile Asp Glu Phe Asn Glu Gly Phe Glu Gly Val
65                  70                  75                  80
 80

Tyr Arg Tyr Leu Glu Met Tyr Thr Asn Lys
                85                  90

(2) INFORMATION FOR SEQ ID NO:2:

(i) SEQUENCE CHARACTERISTICS:
         (A) LENGTH: 90 amino acids
         (B) TYPE: amino acid
         (C) STRANDEDNESS:
         (D) TOPOLOGY: linear (ii) MOLECULE TYPE: protein (vi) ORIGINAL SOURCE:
         (A) ORGANISM: Bacteriophage T4

(xi) SEQUENCE DESCRIPTION: SEQ ID NO:2:

Met Gly Lys Asn Ile Asp Thr Val Arg Glu Ile Ile Thr Val Ala Ser
1               5                  10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Val Ser Glu Leu Thr Gln Glu
    50                  55                  60

Asp Lys Lys Thr Leu Ile Asp Glu Phe Asn Glu Gly Phe Glu Gly Val
65                  70                  75                  80

Tyr Arg Tyr Leu Glu Met Tyr Thr Asn Lys
                85                  90
```

-continued

```
(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: protein (x) PUBLICATION INFORMATION:
        (A) AUTHORS: Amann, E
                     Ochs, B
                     Abel, K-J
        (B) TITLE: Tightly regulated tac promoter vectors
            useful
            for the expression of unfused and fused
            proteins
            in Escherichia coli
        (C) JOURNAL: Gene
        (D) VOLUME: 69
        (F) PAGES: 301-315
        (G) DATE: 1988
        (K) RELEVANT RESIDUES IN SEQ ID NO:3: FROM 1 TO
            20

(xi) SEQUENCE DESCRIPTION: SEQ ID NO:3:

Met Glu Phe Glu Leu Gly Thr Arg Gly Ser Ser Arg Val Asp Leu Gln
1               5                   10                  15

Ala Cys Lys Leu
            20

(2) INFORMATION FOR SEQ ID NO:4:

(i) SEQUENCE CHARACTERISTICS:
        (A) LENGTH: 95 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Met Glu Phe Glu Leu Gly Thr Arg Gly Ser Ser Arg Val Asp Leu Gln
1               5                   10                  15

Ala Cys Lys Leu Asp Thr Val Arg Glu Ile Ile Thr Val Ala Ser Ile
            20                  25                  30

Leu Ile Lys Phe Ser Arg Glu Asp Ile Val Glu Asn Arg Ala Asn Phe
            35                  40                  45

Ile Ala Phe Leu Asn Glu Ile Gly Val Thr His Glu Gly Arg Lys Leu
        50                  55                  60

Asn Gln Asn Ser Phe Arg Lys Ile Val Ser Glu Leu Thr Gln Glu Asp
65                  70                  75                  80

Lys Lys Thr Leu Ile Asp Glu Phe Asn Glu Gly Phe Glu Gly Val
                85                  90                  95

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:5:
```

-continued

```
TAGTCCATGG ATAAAAAGCT TGATACAGTT CGT                            33

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:6:

CTCTAGATAT CGTTATACAC CCTCAAAACC CTCGTTAAAT TCGTC                45
```